United States Patent [19]

Gordon

[11] Patent Number: 4,928,283
[45] Date of Patent: May 22, 1990

[54] X-RAY TOMOGRAPHY APPARATUS

[75] Inventor: Bernard M. Gordon, Magnolia, Mass.

[73] Assignee: Analogic Corporation, Peabody, Mass.

[21] Appl. No.: 160,657

[22] Filed: Feb. 26, 1988

[51] Int. Cl.⁵ .............................................. H05G 1/02
[52] U.S. Cl. ....................................... 378/20; 378/11; 378/196; 250/363.05
[58] Field of Search .............................. 378/4.11–4.14, 378/17, 20, 101, 102, 112, 103, 18, 195, 196, 197, 198; 250/363 SC, 363.05

[56] References Cited

U.S. PATENT DOCUMENTS

| | | | |
|---|---|---|---|
| 3,125,679 | 3/1964 | Ohde et al. | 378/102 |
| 4,138,721 | 2/1979 | Boyd | 378/17 |
| 4,348,590 | 9/1982 | Daniels et al. | 378/115 |
| 4,426,715 | 1/1984 | Baer et al. | 378/4 |
| 4,448,200 | 5/1984 | Brooks et al. | 378/20 |
| 4,472,822 | 9/1984 | Swift | 378/17 |
| 4,651,007 | 3/1987 | Perusek et al. | 250/363 SC |

Primary Examiner—Carolyn E. Fields
Assistant Examiner—David P. Porta

[57] ABSTRACT

Accordingly, the present invention provides an x-ray tomography apparatus having a patient table, x-ray tomography components located around the patient table and in an imaginary plane which intersects the table, and structure for supporting the table and tomography components and including apparatus for moving the tomography components along at least a portion of the table. In an alternate embodiment, an x-ray tomography apparatus includes an annular x-ray tomography system for continuously rotating around a patient, which structure has an electrically powered x-ray source and battery power for supplying electrical power to the x-ray source.

11 Claims, 4 Drawing Sheets

X-RAY TOMOGRAPHY APPARATUS

BACKGROUND OF THE INVENTION

1. Field of the Invention

The present invention generally relates to x-ray tomography apparatuses and, in particular, to those apparatuses which are adapted for CAT scan operations.

2. Statement of the Prior Art

CAT scans (computerized axial tomography) have been used for many years. Generally the system operates by taking multiple, cross-sectional, slice x-rays from different angles within a single plane passing through the body. The results are mathematically compiled to create a cross-sectional image of the body in that plane. To produce these x-rays in one form, an x-ray source and an array of detectors are placed on opposite sides of an annular yoke, which yoke is made to rotate within the selected plane and around the patient.

An important consideration in scanning has been the accurate and consistent alignment of the tomography components and the patient both throughout the rotation and over the course of many scans and patients. Misalignment or movement can negatively influence the data of an entire scan. In order to deal with this factor, manufacturers of CAT scan apparatuses have typically produced a very large and massive machine which includes a heavy yoke for mounting the tomography components. The handling of this weight requires additional mass in the remainder of the apparatus and typically a large apparatus.

One ramification of the extra size and mass of these machines has been the requirement of a patient handling apparatus, as the weight of the patient is typically much less than the weight of the yoke, and other rotating components. Thus, a moveable patient table has been used to properly position the patient in the desired location relative to the fixed yoke, and this further contributes to the size and weight of the apparatus.

A further contibutor to the size and mass of these machines has been the problem of delivering electrical power for the x-ray source to the rotating apparatus. The two approaches primarily used have been electrical brushes, or slip rings, which constantly sweep during rotation and extended cables which limit the rotation of the yoke to approximately one revolution. Unfortunately, the brush approach creates a disruptive amount of electrical interference in the very sensitive output signals of the detectors. Some of this interference can be reduced by the use of shielding; however, the shielding must be extensive as the brushes rotate around the entire large circumference of the yoke. The shielding also adds bulk and weight. More accurate machines use the extended cables which limit rotation. Unfortunately, this approach requires much larger motors and produces greater system stresses and wear, because the yoke and all of the of the moving mass must be accelerated and decelerated quickly in order to adequately operate within the limited rotational range of the yoke.

The apparatus which results from these various requirements is large, heavy, expensive and one which is difficult to relocate. It requires a large amount of floor space and thus cannot be used in space limited environments. A further disadvantage caused by the size and weight of these apparatuses is the wear experienced in the moving parts thereof.

In another form of tomography apparatus known in the prior art, the x-ray source and an array of detectors are mounted on a "C" shaped frame which is typically cantilevered and manipulated over the patient. Although this apparatus can be manipulated over a wide range, it also requires large amounts of space and mass for the manipulation apparatus.

SUMMARY OF THE INVENTION

Accordingly, the present invention provides a tomography apparatus which has a substantially reduced size and mass for enabling a high degree of mobility for the apparatus while requiring a much smaller amount of space for the installation. An x-ray tomography apparatus provides a patient table means, x-ray tomography means located around the patient table means and in an imaginary plane which intersects the table means, and means for supporting the table means and tomography means and including means for moving the tomography means along at least a portion of the table means. In an alternate embodiment, an x-ray tomography apparatus includes an annular x-ray tomography means for continuously rotating around a patient, which means has an electrically powered x-ray source and battery powered means for supplying electrical power to the x-ray source.

The various tomography means of the present invention may be combined with several optional features which further enhance the size, weight, cost and independent movement of the tomography means both rotatively around the patient and otherwise. These optional features includes means for determining the relative position between the patient table means and the tomography means to allow alignment error to be calculated into the data compilation, a non-uniform detector configuration to reduce the number of detector channels used, and means for providing wireless transmission of the tomography data.

BRIEF DESCRIPTION OF THE DRAWINGS

The present invention is illustratively described with respect to the accompanying drawings in which.

DETAILED DESCRIPTION OF THE DRAWINGS

Figure 1:
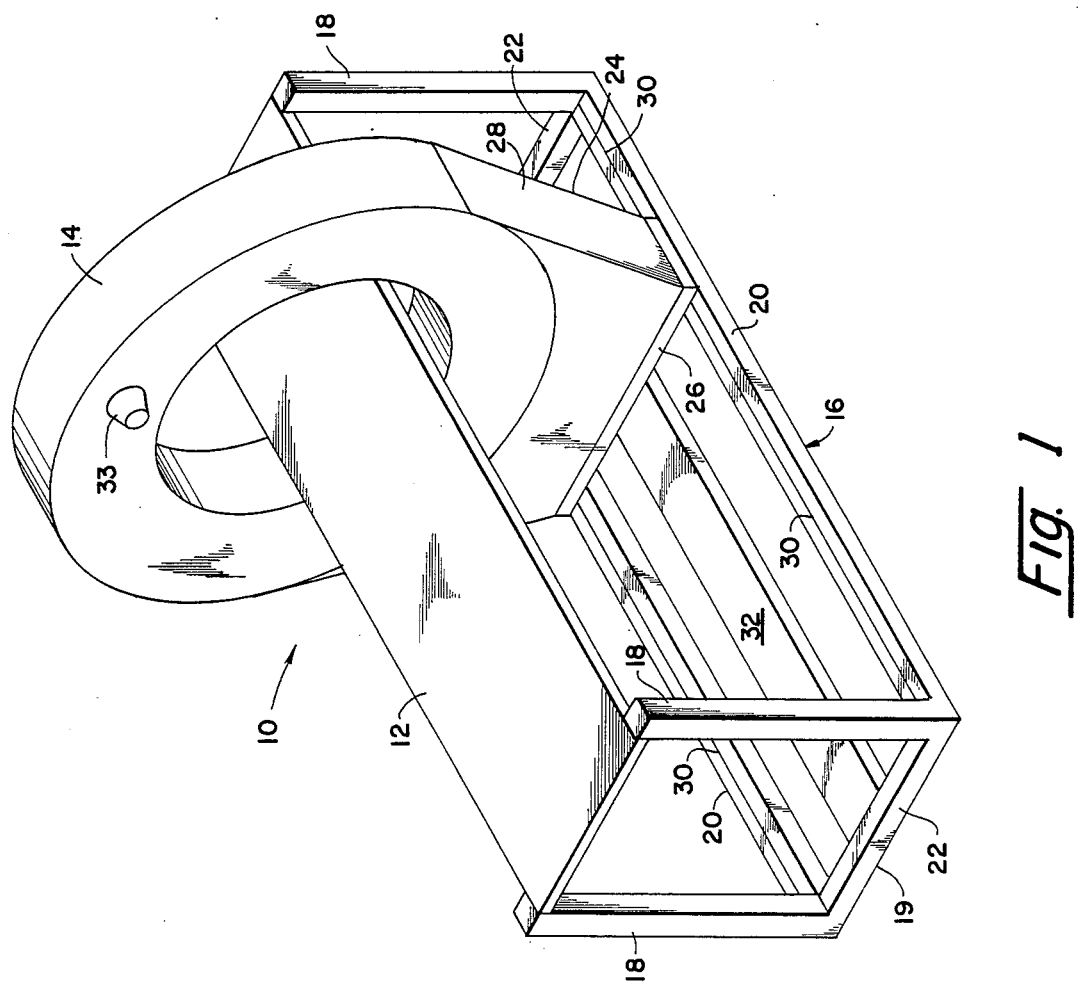
FIG. 1 is a perspective view of an x-ray tomography apparatus constructed in accordance with one embodiment of the present invention.

FIG. 1 shows an x-ray tomography apparatus 10 generally including a patient table 12, a tomography apparatus 14, and a support structure 16 for the table 12 and the tomography apparatus 14. The patient table 12 is intended to be removable from the support structure 16. Support structure 16 may take any suitable form capable of performing the functions described herein. As shown, structure 16 includes four vertical support members or legs 18 connected to a floor bracket 19 including side members 20 and end members 22.

Also included in the support structure 16 is a cradle 24 for supporting the tomography means 14. Cradle 24 includes a lower cradle member 26 and an upper cradle member 28. Lower cradle member 26 is supported at each end thereof by the side members 20 of the support structure 16. This support is provided through bearing surfaces 30 to allow the support means 24 and the tomography means 14 to be moved at least a portion of the length of the patient table 12. To effect this movement, a drive means 32 is coupled between end members 22 and engages the lower cradle member 26. Drive means 32 may comprise any means capable of moving the cradle and tomography means 14 the required distances. One suitable means would be a worm gear engaging a portion of the lower cradle member 26. Another would be a drive belt. In a preferred embodiment the drive means 32 is adapted to move the tomography means the entire length of the table 12. This would allow the apparatus to be used in an operating room setting where the tomography means 14 would be stored at a patients feet when not in use and thus not be in the way of surgeons or the anesthetist.

Figure 2:
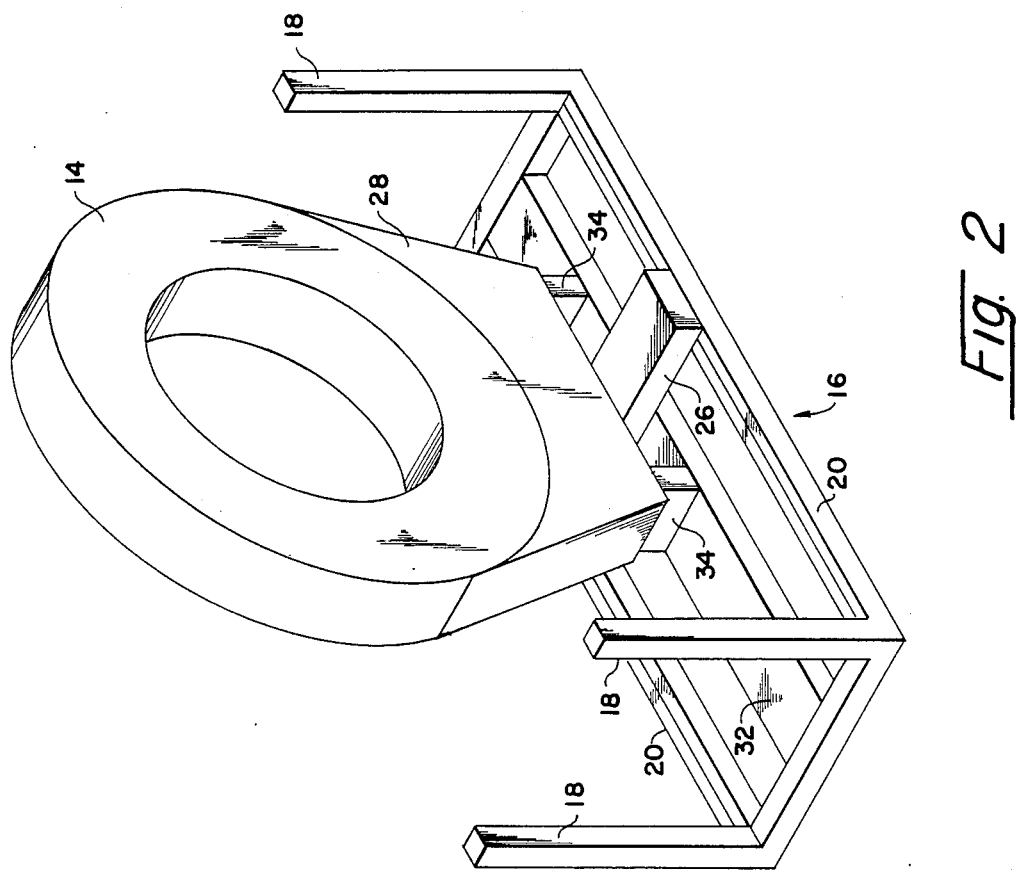
FIG. 2 is a perspective view of a different orientation of the apparatus of FIG. 1.

Cradle 24 is constructed with upper member 28 rotatably mounted to lower member 26 to enable upper member 28, and therefore the tomography means 14, to be rotated to a position parallel with the length of the table as shown in FIG. 2, for enabling easier transportation of the apparatus 10. To further this function, a pair of removable support blocks 34 are mounted on drive means 32 to steady the tomography apparatus in the transport position. Also, the legs 18 may be stiffened by diagonal members (not shown) affixed to the end members 22, and wheels may also be mounted to the floor bracket 19. During transport the table 12 would be removed from the support 16 and the tomography means 14 would be turned to the position shown in FIG. 2 which is substantially parallel to the length of the support 16.

FIG. 1 also shows means 33 for determining the position of the tomography means 14 with respect to the table 12. This function may be performed by an suitable means such as some form of optical measurement system. The system may be mounted on the tomography means 14 at 33 as shown in FIG. 1 and make reference to the table 12, or it may be mounted on the table 12 and make reference to the tomography means 14. Special measurement markings or indicia may also be mounted on either the tomography means 14 or table 12 for reference to by the system. The measurement system could provide information on both the angular position of the tomography means 14 and any misalignment thereof within the rotational plane. All of this information can be used in compiling images from the scan data. Thusly, misalignments during the scan could be used to provide more scan data for the construction of images because they would reduce the amount of duplicate data collected during the scan.

Figure 3:
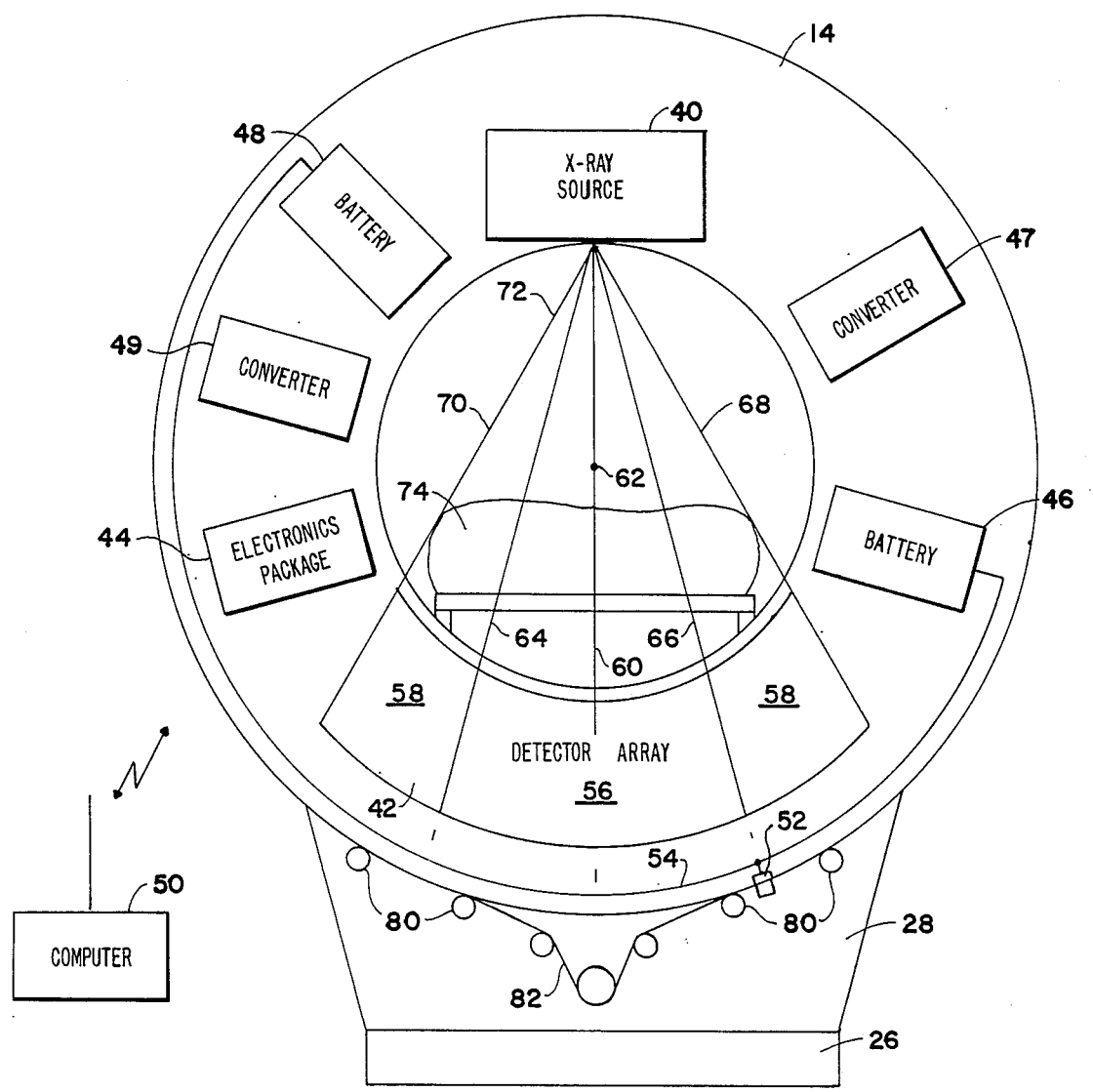
FIG. 3 is a sectional view of the apparatus of FIG. 1 taken along view lines 2—2.

FIG. 3 is a sectional view of the apparatus of FIG. 1 taken along view lines 3—3 and showing greater detail of the tomography means 14. Whereas the tomography means 14 may have various covers affixed thereto for providing a more esthetic apparatus, the would be covers are removed in FIG. 3 to allow a representational showing of the instrumentation. Tomography means 14 is shown to include a number of tomography components including an x-ray source 40, an array of detectors 42, a control and data handling electronics package 44, a source of power for the x-ray source 40 including batteries 46 and a power converter 47, and a source of power for the electronics package 44 including batteries 48 and a power converter 49. It is anticipated that the tomogrphy means 14 will have a patient opening or inner diameter of approximately 65 to 70 centimeters and an outer diameter of approximately 125 to 140 centimeters.

X-ray source 40 provides for the electrical generation of x-rays by methods well known in the art. In a preferred embodiment the x-ray source 40 is adapted for continuous operation during a scanning operation. This technique of scanning is referred to as Continuous Wave Fan Beam Tomography and is described in greater detail in U.S. Pat. No. 4,547,893, assigned to Analogic Corporation of Peabody, Mass. This technique reduces the signal processing electronics necessary with attendant cost and weight savings. X-ray source 40 would also include a collimator for determining the x-ray fan beam and means for dissipating excess heat generated in the production of the x-rays.

The electronics package 44 provides for data handling from the detectors 42 and for control of the x-ray process. This control is provided via a two-way communication link between the electronics package 44 and a computer 50 used for image processing and control. This two-way communication link may be achieved by any suitable means. Further, the control and image processing methods which may be used by computer 50 are well known in the CAT scanning art.

Power for the x-ray source 40 and for the data handling electronics package 44 is provided from the batteries 46 and 48 and the power converters 47 and 49, respectively. These power converters 47, 49 provide the voltages necessary for the respective equipment which they power. Power converter 47 is a high-voltage supply, and power converter 49 is a low voltage supply. Whenever the tomography means 14 is brought to the rest position in between scans, shown in FIG. 3, a pair of electrical contacts 52 may be used to recharge the batteries 46 and 48 in order to allow pseudo-continuous operation of the CAT scan. These contacts 52 are shown to be connected to the batteries 46 and 48 via electrical lines 54. Converters 47, 49 would also include means for dissipating excess heat generated in the conversion process.

The detector array 42 includes three sections of detectors 56 and 58. The section 56 is located about a center line 60 which passes through the x-ray source 40 and through the center of rotation 62 of the tomography means 14. The section 56 of detectors is substantially centered on either side of the center line 60, with perhaps a small offset to avoid symetry about the center line 60 for providing greater amounts of collected data. The x-rays which strike the detectors within section 56 radiate along the radial lines located between radial lines 64 and 66 passing from the x-ray source 40 to the detector array 42. The other sections 58 of detectors are located adjacent to the section 56 and are intended to receive x-ray information for x-rays radiating between the radial lines 66 and 68, 64 and 70 from the source 40. Thusly, energy is only radiated from the source 40 within the fan beam 72 located between radial lines 68 and 70.

The purpose of having two groups of detectors concerns the informational content of the x-rays being detected. Within the radial lines 64 and 66 are typically located all of the major organs and complex structure of the human body. The body structure located between radial lines 66 and 68, 64 and 70 is typically much simpler and does not encompass vital organs. Therefore the informational content of the x-rays between lines 64 and 66 is greater and more important than the informational content of the x-rays between lines 66 and 68, 64 and 70. For this reason, it is permissible to construct an array of detectors which has higher detector density in the section 56 and a lower detector density in the section 58. This allows a reduction, and therefore a cost and weight savings, in the number of detectors and the associated electronics used where the information to be collected simply is not present. In lieu of and/or in combination with varying detector densities, it may be desireable to sample the outer detectors 58 at a lower rate than the inner detectors 56. It may also be desireable to have more than two groups of detectors having different detector densities and/or sampling rates. This technique is discussed in greater detail in U.S. Pat. No. 4,677,554, also assigned to Analogic Corporation.

It should be noted that it is possible to construct the tomography means 14 without having any detectors located to the left of section 56. When the tomography means 14 is in the position shown in FIG. 3, data is not collected for those portions of the body 74 which lie to the left of radial line 64. Those portions 74 of the body are x-rayed as the tomography means 14 rotates through other angular positions with respect to the patient. Again, because this outer portion 74 contains no vital organs, the data to be collected therefrom is less significant and the structure can be imaged by using less data collection. The elimination of this additional section of detectors enables further weight and cost savings for the x-ray apparatus.

Also shown in FIG. 3 are means for rotatably supporting and for rotating the tomography means 14. Any suitable means may be used for this purpose. Nominally shown in FIG. 3 are roller bearings 80 and a drive belt apparatus 82. These means are capable of continuously rotating the tomography means 14 without stopping to collect data for individual scans. Continuous rotation enables the use of the Continuous Wave Fan Beam Tomography technique referred to above. Continuous rotation is possible because the tomography means is designed and constructed to be electrically independent. It is anticipated that the tomography means 14 will rotate at a speed of approximately one revolution every 4 to 5 seconds or 12 to 15 revolutions per minute.

Figure 4:
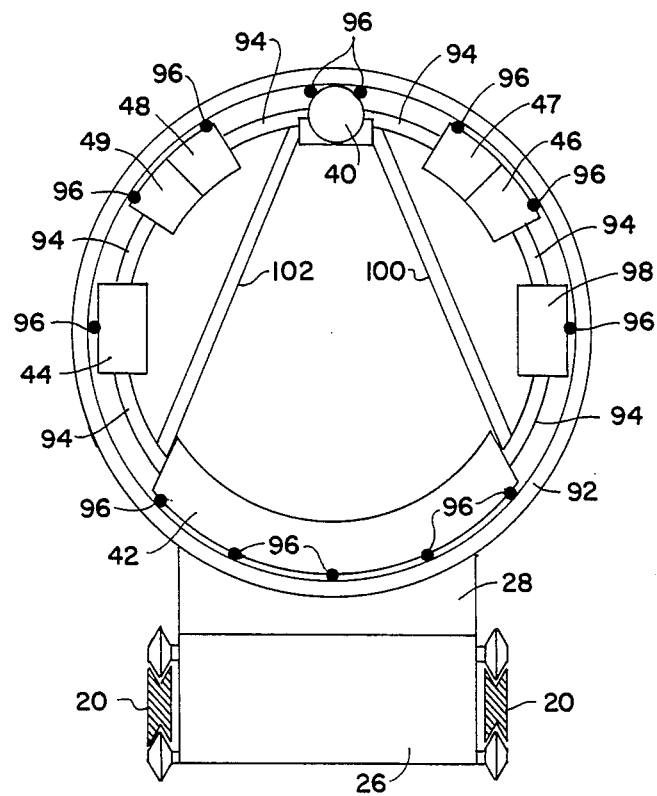
FIG. 4 is a side view of an alternative embodiment of a portion of the apparatus of FIG. 1.

FIG. 4 shows an alternate embodiment 90 of tomography means 14 with the addition of a circular frame or track 92 which is stationary and surrounds the tomography components. The tomography components are both connected and held apart by a multiplicity of hollow separators 94 through which electrical cables are run. The separators 94 are used to physically bias the components apart and thus outwardly against the track 92. The components engage the track 92 by means of wheels 96. The track 92 thereby helps to provide rigidity to the tomography means 90.

Further disclosed in FIG. 4 as one of the tomography components is a means 98 for rotating the tomography means 90 within the circular track 92. This means 98 is an electrically powered locomotive means which might be powered by its own internal battery or any other suitable means. Locomotive means 98 engages the track 92 by any suitable means such as a gear-and-tooth arrangement, and similar to the tomography means of FIG. 3, enables continuous rotation thereof. The remainder of the components of tomography means 90 of FIG. 3 are identical to those of the tomography means 14 of FIG. 3.

Also included as part of the structure of the tomography means 14 are a pair of triangularly placed support members 100 and 102. The upper ends of members 100 and 102 are coupled to the x-ray source 40, preferably at a single coupling point(not shown). The lower ends of members 100 and 102 are connected to opposite ends of the detector array 42. The detector array 42 is mounted on a rigid structure so that the ends thereof do not move with respect to one another. The distances between the ends of the detector array 42 and the x-ray source describe a triangle which may either be equilateral or have an angle greater than 60 degrees at the corner of x-ray source 40. The equilateral triangle would provide the most clearance for the patient and table 12 if the sides of the triangle were straight. Because the detector array 42 is arcuate a non-equilateral triangle may be used. Thus, the members 100 and 102 and detector array 42 form a pseudo-triangular structure for significantly enhancing nthe rigidity of the tomography means 90. This arrangement helps to provide both the proper alignment between the x-ray source 40 and the detector array 42 and also lends signficiant rigidity to the annular shape of the tomography means 90 which might otherwise be distorted during rotation.

METHOD OF OPERATION

During scanning of a patient, the apparatus of the present invention may be operated in any one of several modes. The most typical mode of operation would be to locate the tomography means 14 along the patient table 12 by use of the drive means 32 at the desired position with respect to a patient located on the table 12. This may be accomplished by visual reference to the patient. When the tomography means 14 is properly located, it is rotated to perform a set of scans in accordance with the continuous wave tomography method. Signals to perform this scan are transmitted from the computer 50 to the electronics package 44, which then takes control of the operation.

The present apparatus may also be used to produce a simple x-ray of a patient in what may be termed a scout mode. To accomplish this, the tomography apparatus 14 is not rotated but moved along the table 12 while the x-raying is performed. The data collected from this operation is used to produce a normal x-ray of the patient, such as that which might be used to determine the general location of specific organs and other points. As the fan beam of x-rays shown in FIG. 3 does not cover the entire patient, and in particular the portion 74, it would simply be necessary to rotate tomography means 14 until the width of the fan beam at the center of rotation 62 were sufficient to encompass the entire body prior to performing the scout scan of the patient. Such simple x-rays may also be effected by scanning the patient twice, first with the position of the tomography means shown in FIG. 3, and then again with the tomography means 14 inverted to cover the portion 78 of the patient. This method would produce an enchanced image for the area covered by detector section 56.

Lastly, it is possible to perform a helical scan of the patient by simultaneously rotating the tomography means 14 and moving it along the patient table 12. This scanning method allows three dimensional data to be collected, from which data it would be mathematically possible to construct an image for any slice through the scanned volume. Thus a patent's head could be scanned as a volume and the radiologist would have available any image of the head that he or she might want. This would avoid the necessity of bringing a patient back for additional x-rays when more information is desired.

The embodiments of the present invention described are intended to be taken in an illustrative and not a limiting sense. Various modifications and changes may be made to these embodiments by persons skilled in the art without departing from the scope of the present invention as defined in the appended claims.

What is claimed is:

1. An x-ray tomography apparatus, comprising:
   an elongated patient table means having opposite ends;
   a rotary fan beam x-ray tomography means encircling the patient table means; and
   means for supporting the table means at opposite ends thereof and for supporting the tomography means from underneath and including means for moving the tomography means along a substantial portion of the table means,
   wherein the tomography means includes means for causing at least a portion of the tomography means to continuously rotate around the table means.

2. The apparatus of claim 1, wherein the tomography means comprises a multiplicity of members including an x-ray source, an array of detectors, tomography electronics and at least one means for supplying electrical power for the tomography means.

3. The apparatus of claim 2, further comprising means for physically interconnecting the members of the tomography means in an annular shape for rotation around the table means.

4. The apparatus of claim 3, wherein the tomography means further includes triangularly placed structural members affixed between the x-ray source and the array of detectors.

5. The apparatus of claim 4, wherein the array of detectors includes a support member which extends between the triangularly placed structural members.

6. The apparatus of claim 2, further comprising means for transmitting control and data signals to and from the tomography means.

7. The apparatus of claim 2, wherein the means for supplying electrical power are battery powered.

8. The apparatus of claim 2, wherein the rotation of the tomography means defines a center of rotation thereof and further wherein the array of detectors include at least first and second groups of detectors with the first group being substantially centered about an imaginary line passing through the x-ray source and the center of rotation and the second group being located adjacently to the first group.

9. The apparatus of claim 8, wherein the first group of detectors has a higher average detector density than the second group.

10. The apparatus of claim 1, further comprising means for determining the relative position between the tomography means and the patient table means.

11. The apparatus of claim 1, wherein the means for supporting is elongated and the table means is removeable from the means for supporting, and further wherein the means for supporting includes means for allowing orientation of the tomography means to a position where an imaginary plane of rotation defined by the rotating portion of the tomography means is substantially parallel with the elongated means for supporting.

* * * * *

UNITED STATES PATENT AND TRADEMARK OFFICE
CERTIFICATE OF CORRECTION

PATENT NO. : 4,928,283
DATED : May 22, 1990
INVENTOR(S) : Bernard M. Gordon

It is certified that error appears in the above-identified patent and that said Letters Patent is hereby corrected as shown below:

Claim 8, column 8, lines 13 and 14, delete "include" and substitute therefor --includes--;

Claim 11, column 8, lines 26 and 27, delete "removeable" and substitute therefor --removable--.

Signed and Sealed this

Twenty-second Day of October, 1991

Attest:

HARRY F. MANBECK, JR.

*Attesting Officer*  *Commissioner of Patents and Trademarks*